United States Patent
Sander

(10) Patent No.: US 6,592,086 B1
(45) Date of Patent: Jul. 15, 2003

(54) MICROSCOPE STAND HAVING X-Y-Z ADJUSTMENT UNIT

(75) Inventor: Ulrich Sander, Rebstein (CH)

(73) Assignee: Leica Microsystems AG, Heerbrugg (CH)

(*) Notice: Subject to any disclaimer, the term of this patent is extended or adjusted under 35 U.S.C. 154(b) by 0 days.

(21) Appl. No.: 10/189,794

(22) Filed: Jul. 8, 2002

(30) Foreign Application Priority Data

Jul. 6, 2001 (DE) .......................................... 101 33 018

(51) Int. Cl.[7] .................................................. A47F 5/00
(52) U.S. Cl. ............................... 248/123.11; 206/316.1; 248/278.1
(58) Field of Search .................. 248/123.11, 278.1, 248/280.11, 281.11, 648, 187.1; 359/385, 388, 368, 390, 392; 206/316.1

(56) References Cited

U.S. PATENT DOCUMENTS 5,213,293 A * 5/1993 Muentener et al. ..... 248/123.11
5,667,186 A * 9/1997 Luber et al. ................. 248/550
5,713,545 A * 2/1998 Nakamura ............... 248/123.2
5,818,638 A * 10/1998 Nakamura ................... 359/384
6,471,165 B2 * 10/2002 Twisselmann ......... 248/123.11

FOREIGN PATENT DOCUMENTS

WO          00/08508      2/2000

OTHER PUBLICATIONS

"Motion Control", 2000 Catalog, Newport, pp. 2–22, 2–34, 3–6, 4–8, and 5–10.

US 2002/0108874 A1, inventor Metelski, Publication Date Aug. 15, 2002, filing date Sep. 27, 2001.*

* cited by examiner

Primary Examiner—Ramon O. Ramirez
(74) Attorney, Agent, or Firm—Foley & Lardner

(57) ABSTRACT

A stand, in particular for surgical microscopes, in which motor-activated balancing adjustment systems provide additional positioning capability in the three spatial axes X, Y, and Z.

14 Claims, 3 Drawing Sheets

MICROSCOPE STAND HAVING X-Y-Z ADJUSTMENT UNIT

CROSS REFERENCE TO RELATED APPLICATIONS

This application claims priority of the German patent application 101 33 018.9.

FIELD OF THE INVENTION

The invention concerns a microscope stand used, for example, in connection with surgical microscopes.

BACKGROUND OF THE INVENTION

Many conventional stands—e.g. those for surgical microscopes for ophthalmology—carry at their free end, between the microscope and the vertical stand support, an X-Y displacement unit for the microscope. This displacement unit serves to position the microscope to within millimeters in the X-Y direction. This kind of arrangement of the X-Y displacement unit is usually troublesome to an operator, since a large mass and a large volume must be moved. It also makes it difficult to meet the necessary sterility requirements. The X-Y displacement unit furthermore considerably increases the weight on the extension arm, and usually must be compensated for using an appropriate counterweight, or supported with an appropriately large stand foot. As a consequence, the entire carrier arm structure of the stand support, and optionally also the entire stand foot structure, must therefore be of larger dimensions or cover a greater area.

The object of a patent application of Leica Microsystems AG (WO-A-00/08508) was therefore to discover a stand configuration in which the X-Y adjustment function is retained but any considerable weight increase in the carrier arm structure, and the further disadvantages resulting therefrom, are avoided.

The manner in which this earlier object was achieved was not intended necessarily to be limited to a linear adjustment in two stages occurring one after another, or in general to a linear displacement. It also encompassed any desired motions, e.g. calculated or controlled curves, rotary, or pivoting motions in a horizontal plane, and optionally also Z (vertical) adjustments.

The earlier object was achieved, in accordance with the invention, by relocating the X-Y displacement unit at least closer to the vertical stand column, so that the X-Y positioning unit moves not only the microscope but also at least a portion of the horizontal stand support.

In the WO-A application, the X-Y displacement unit was not necessarily limited to slide-like displacement tracks. It could also, for example, comprise at least two motor-driven joints of the horizontal stand support whose mutually coordinated pivoting motions allow an arbitrary change in the position of the microscope in an X-Y plane.

These were features that have proven successful in surgical microscopes in ophthalmology, where (as already mentioned above) what is important is the greatest possible precision in X-Y positioning of the microscope especially during an operation, the consideration here being known surgical techniques used in ophthalmology. In a preferred embodiment, these were implemented using a planar motorized X-Y adjustment system that is not placed directly above the microscope. In the assemblage according to the WO-A application, the microscope itself was not located on a pivot support, and its position therefore was modified practically only by way of the X-Y adjustment system or by pivoting the stand carrier arm.

In ear, nose and throat medicine (ENT) or neurology, on the other hand, what is required is not so much maximum accuracy in the X-Y adjustment, but rather smooth operation (with one hand, if possible) of the microscope on, for example, a pivot support. In this respect, knowledge from microscopy as applied in ophthalmology offers no assistance for stands in the ENT field.

The Applicant has succeeded in specifically serving this market with a surgical microscope (M400-E) that is equipped with a manual X-Y-Z adjustment system and a pivot support. With these it is possible to bring the microscope, by itself or with its various adapters and/or accessories, into a balanced-out position in which the requisite smooth one-hand operation is then guaranteed.

A microscope is balanced when the microscope body is at the center of gravity of the supporting structure. In such a state, the microscope body is easily moveable by hand.

SUMMARY OF THE INVENTION

Proceeding from existing art, the question arises as to whether the position adjustment systems of the ophthalmological microscope and the balancing adjustment systems of the ENT microscope can be improved and speeded up, and whether the laborious (manual) balancing-out of the microscope could be simplified and made more efficient.

The present invention is directed to the manner of achieving the aforesaid object. The present invention makes it possible to reduce the weight and volume on the load arm of the stand, and in that way to improve the stand structure and make it smaller. Any compensation devices that may be present, and optionally also the stand foot, are made lighter and reduced in size.

This object was thus achieved according to the present invention by using the manual X-Y adjustment system, intended for balancing, in such a way that it retains its previous balancing function but additionally has a new and "alien" task imposed upon it. This new task is the positioning of the microscope body in three dimensions and above the specimen to be examined. According to the present invention, the manual balancing adjustment system of the M400-E is now designed as a motorized position adjustment system. This was done by designing the manual X-Y-Z carriage displacement system built into the M400-E as a motor-activated planar X-Y adjustment system and motor-driven Z adjustment system (focusing system).

The result was to create a surgical microscope which can be moved smoothly and with one hand in a balanced-out state, but at the same time can also be adjusted exactly and quickly in motorized fashion, and retained in (possibly unbalanced) position by the mechanical resistance of the motors.

Also part of the invention is the fact that in a particular embodiment, the Z axis is also integrated in the form of a motor-driven focusing system.

The advantages of the innovation according to the present invention include the aforementioned increased speed and efficiency, but also a very compact design, since a separate X-Y coupling is rendered obsolete. The reason is that depending on the configuration and placement of the X-Y adjustment system, in some circumstances all that remains on the microscope body is the motorized focusing system. According to the present invention, the remaining parts are integrated into the mount (support), but in any case in the vicinity of the microscope body.

Numerous embodiments and arrangements of the X, Y, and Z control systems are conceivable. According to a preferred embodiment of the invention, the adjustment capability along the Y and Z axes is arranged directly on the microscope body, and the X adjustment system is located on the pivot support above the microscope.

According to a further improvement, a computer (not depicted in further detail) in conjunction with suitable sensor elements serves to sense the current position of the microscope with reference to the specimen or to a patient, and to convert the respective X-Y-Z command values in such a way that the adjustment motion that is executed is performed, for example, in the X-Y-Z coordinate system of the specimen or patient, or in the coordinate system of the microscope, regardless of the microscope's pivot position in space; or in order to ascertain and (if necessary) correct the balance situation.

According to a further embodiment of the invention, the adjustment devices can also be incorporated into a ceiling mount. The range of protection would thus also extend thereto; the term "column" or "stand" would then be understood as to include a suspended support, and "foot" would be understood as any stand base on the floor, wall, or ceiling.

According to a further embodiment, the adjustment units can be configured so they can be decoupled, so that manual operation is possible.

A further preferred embodiment provides for electric motors with integrated incremental transducers to be used. This allows reference coordinates of a specific desired or balanced-out position to be moved to automatically.

Further features of the invention, and variant embodiments, are described below. Further features and patentable details are also evident from the Figures and the description thereof.

BRIEF DESCRIPTION OF THE DRAWINGS

The description of the Figures is overlapping. Identical reference characters denote identical components; reference characters with different indices denote components with identical purposes but different physical configurations.

In the drawings.

DETAILED DESCRIPTION OF THE INVENTION

Figure 1:
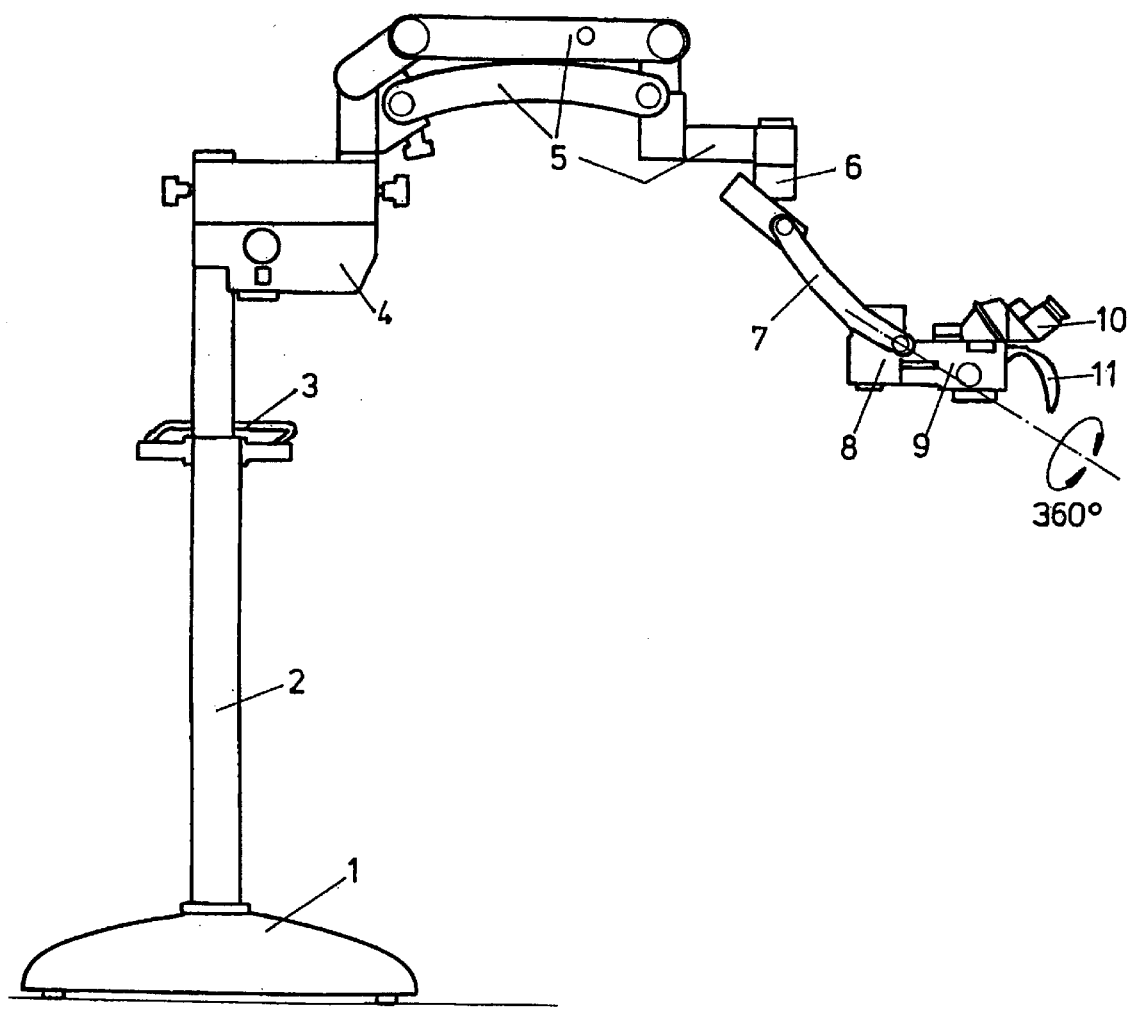
FIG. 1 is a schematic view of the overall configuration of a surgical microscope with the stand foot, vertical support, control unit, horizontal supports, pivot support, and microscope unit.

FIG. 1 is a schematic view of an overall configuration of a surgical microscope according to the present invention. A stand foot 1, from which a vertical support 2 projects, is evident. For convenient movement of the stand (which is mounted on casters), a handle 3 is attached to vertical support 2. Mounted on vertical support 2 is a control unit 4 on which horizontal supports 5 are supported. Control unit 4 supplies electric components (motors, X, Y, and Z adjustment units, lamps, zoom, focus adjustment, speed control adjustment, and the like) with electronic control signals. In the embodiment depicted, the horizontal supports end in X adjustment unit 6 which, inclusive of pivot support 7, moves microscope body 9 mounted thereon in the X axis. Y adjustment system 8 is located at the other end of pivot support 7. Also depicted are the binocular tube with eyepieces 10, and an ergonomically shaped grip 11.

Figure 2:
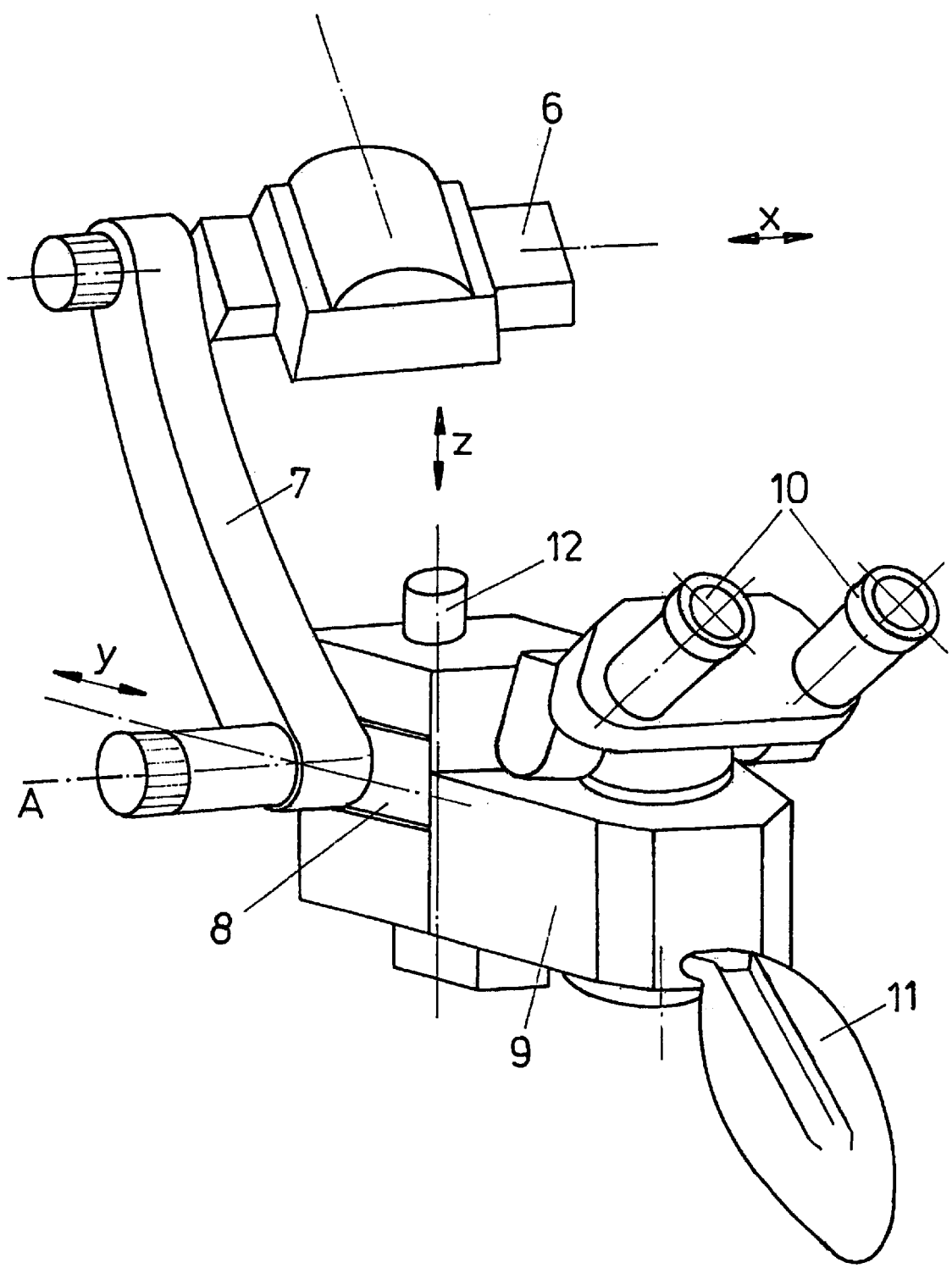
FIG. 2 is a schematic perspective view of a symbolic configuration of the adjustment units, the pivot support, the microscope unit, and a grip for comfortable one-hand movement.

FIG. 2 depicts in perspective fashion the configuration of the surgical microscope in the vicinity of the actual microscope body 9. X adjustment unit 6 is depicted at the upper end of pivot support 7, and the adjustment unit for the Y axis 8 is located at the lower end. A Z adjustment system 12 is simultaneously depicted here as well. Once again, what is visible of the microscope itself are body 9, the binocular tube with eyepiece tubes 10, and the ergonomically shaped grip 11.

Figure 3:
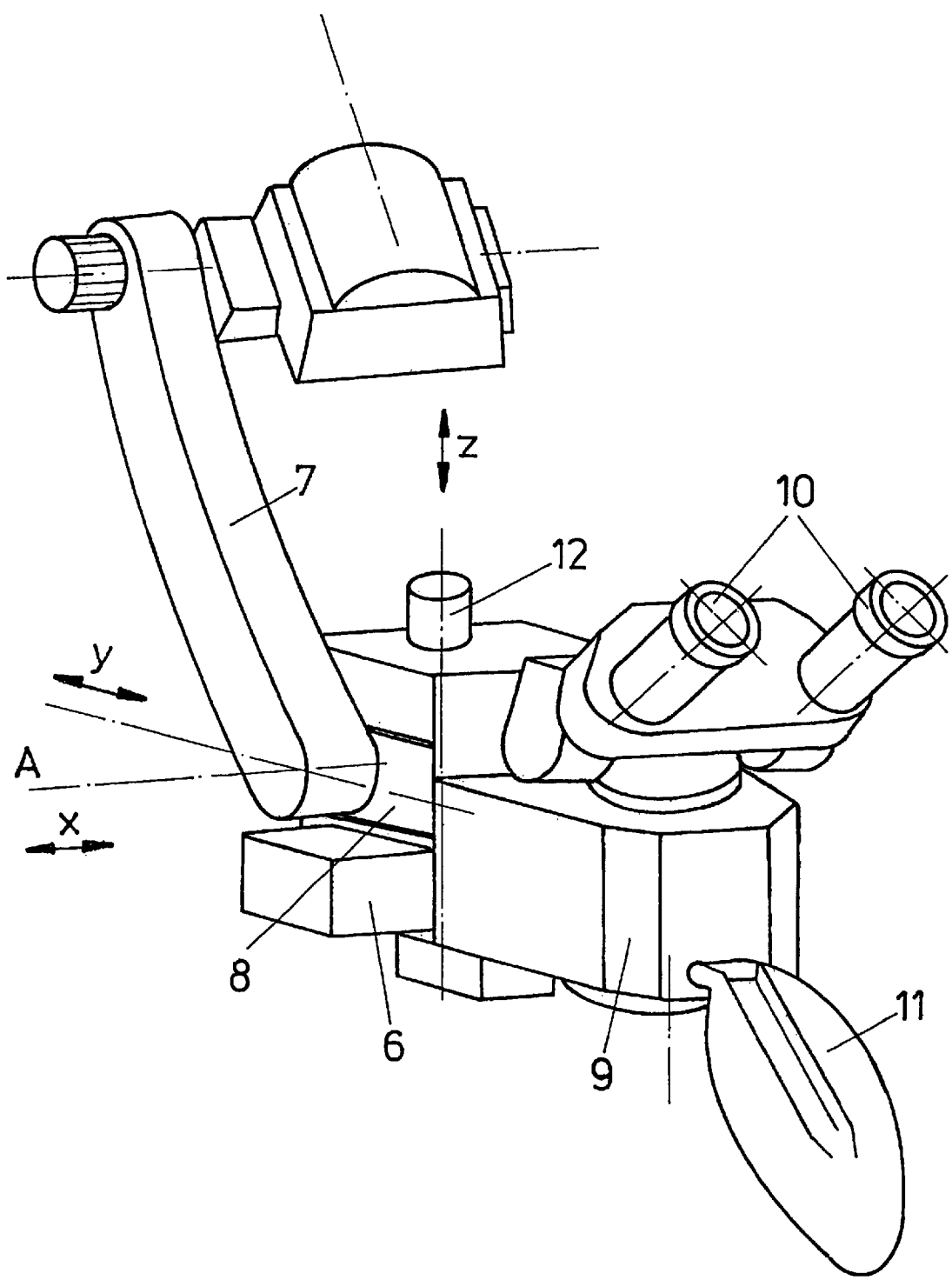
FIG. 3 is a schematic view of a configuration as shown in FIG. 2, with the difference that the X adjustment system is arranged in axis A.

FIG. 3 shows a different mounting location for the X adjustment unit, namely (like the Y and Z adjustment systems) directly on the microscope body along axis A.

When the surgical microscope is in use, the three adjustment systems intended for balancing thus ensure that the microscope can be positioned and that motions can be performed in all three principal axes. The three principal axes are to be understood as follows: the X axis as a motion direction approximately to the viewer's left and right, the Y axis as a motion direction forward and backward, and the Z axis as a motion direction oriented up and down. Any imaginable movement in three dimensions can, of course, be performed by means of the one-handed grip by combined operation of the adjustment units coupled with a 360-degree rotation capability of the microscope body.

Suitable adjustment systems include, for example, motorized translation stages, linear motor stages, multi-axis motion controllers, motorized steppers, DC servo actuators, rotation stages, as well as other types of adjustment systems. Such systems are available from, for example, Newport Corporation (Irvine, Calif.). This company's 2000 catalog entitled "Motion Control" is incorporated herein by reference in its entirety.

The Parts List below is a constituent of the Specification. The assemblages, devices, and details recited in the Claims are also considered to be disclosed in the context of the Specification.

PARTS LIST

1 Stand foot
2 Vertical support
3 Grip
4 Control unit
5 Horizontal supports
6 X adjustment unit
7 Pivot support
8 Y adjustment unit
9 Microscope body
10 Eyepiece
11 Handle
12 Z adjustment unit
A Axis
X X axis
Y Y axis
Z Z axis

What is claimed is:

1. A stand for a surgical microscope, comprising:
a stand foot;

a vertical support;

at least one horizontal support;

a pivot support; and an X-Y-Z adjustment unit with the pivot support having motor-activated X, Y and Z adjustment units, wherein the X, Y, and Z adjustment units are configured to position a microscope body in three dimensions to retain the microscope body in position in an unbalanced state by mechanical resistance of motors.

2. The stand of claim 1, wherein the motorized Z adjustment unit comprises a focusing system.

3. The stand of claim 1, wherein the motorized X adjustment unit is arranged above the pivot support.

4. The stand of claim 1, wherein the motorized X adjustment unit is arranged on a microscope body.

5. The stand of claim 1, wherein an X-Y adjustment can be performed by actuating motors such that a separate X-Y coupling is omitted.

6. The stand of claim 1, further comprising:

a computer adapted to coordinate the X, Y, Z adjustment unit, and to sense pivot motions of a microscope body about its own vertical axis or about a vertical axis of the stand, wherein in the case of an X-Y adjustment, the computer is adapted to take into account that for a user, the X-Y direction is always the same with reference to a specimen or a patient.

7. The stand of claim 1, wherein the X, Y, and Z adjustment units are adapted to be decoupled in a manual mode.

8. The stand of claim 1, wherein the stand foot is adapted to mount on a ceiling.

9. The stand of claim 1, wherein the stand foot is adapted to mount on a wall.

10. The stand of claim 1, wherein at least one of the motor-activated adjustment units includes an electric motor having integrated incremental transducers adapted to automatically move a microscope body to a predetermined position of specified reference coordinates.

11. The stand of claim 1, wherein the X-Y-Z adjustment unit is incorporated into a balancing unit.

12. The stand of claim 1, wherein the X-Y-Z adjustment unit is an X-Y-Z balancing unit.

13. A microscope stand, comprising:

a stand foot;

a vertical support connected to the stand foot;

at least one horizontal support, wherein the at least one horizontal support is connected to the vertical support;

a pivot support connected to the at least one horizontal support; and an X-Y-Z adjustment unit for balancing in a pivot support having:

a motor-activated X adjustment unit;

a motor-activated Y adjustment unit; and a motor-activated Z adjustment unit, wherein the X-Y-Z adjustment unit is adapted to position a microscope body in three dimensions and to retain the microscope body in position in an unbalanced state by mechanical resistance of motors.

14. A method of X-Y-Z positioning of a microscope body above an object comprising the steps of:

providing an unbalanced microscope body;

providing an X-Y-Z balancing adjustment unit;

providing motors;

driving the X-Y-Z balancing adjustment unit with the motors to position the microscope body in three dimensions; and retaining the microscope body in an unbalanced state by mechanical resistance of motors.

* * * * *